(12) United States Patent
Weinberg

(10) Patent No.: US 11,826,276 B2
(45) Date of Patent: Nov. 28, 2023

(54) OUTLET CLOSURE AND SECUREMENT SYSTEM FOR DRAINABLE POUCH

(71) Applicant: Hollister Incorporated, Libertyville, IL (US)

(72) Inventor: Robert J Weinberg, Lake Villa, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/252,288

(22) PCT Filed: Jan. 12, 2023

(86) PCT No.: PCT/US2023/060551
§ 371 (c)(1),
(2) Date: May 9, 2023

(87) PCT Pub. No.: WO2023/147220
PCT Pub. Date: Aug. 3, 2023

(65) Prior Publication Data
US 2023/0320890 A1    Oct. 12, 2023

Related U.S. Application Data

(60) Provisional application No. 63/304,998, filed on Jan. 31, 2022.

(51) Int. Cl.
*A61F 5/44* (2006.01)
*A61F 5/445* (2006.01)
(Continued)

(52) U.S. Cl.
CPC ............ *A61F 5/4407* (2013.01); *A61F 5/445* (2013.01); *A61F 5/441* (2013.01); *A61F 5/442* (2013.01); *A61F 5/443* (2013.01)

(58) Field of Classification Search
CPC ........ A61F 5/4407; A61F 5/441; A61F 5/442; A61F 5/443; A61F 5/445
See application file for complete search history.

(56) References Cited

U.S. PATENT DOCUMENTS 2,520,831 A * 8/1950 Chincholl ............... A61F 5/445
                                                       604/335
3,655,118 A * 4/1972 Rinecker ................. A44B 18/00
                                                       383/62
(Continued)

FOREIGN PATENT DOCUMENTS

EP    1033951 B1    3/2004
EP    1221916 B1    12/2004
(Continued)

OTHER PUBLICATIONS

International Search Report issued by ISA/EPO in connection with PCT/US2023/060551 dated Mar. 20, 2023.
(Continued)

*Primary Examiner* — Guy K Townsend
(74) *Attorney, Agent, or Firm* — Levenfeld Pearlstein, LLC

(57) ABSTRACT

A drainable pouch including an outlet closure and securement system is provided. The outlet closure and securement system include at least one tab and a cover including at least one slot. The drainable pouch is closed by folding up an outlet portion, wherein the folded up outlet portion is secured to and hidden behind the cover when the at least one tab is received in the at least one slot.

16 Claims, 3 Drawing Sheets

(51) Int. Cl.
*A61F 5/443* (2006.01)
*A61F 5/442* (2006.01)
*A61F 5/441* (2006.01)

(56) References Cited

U.S. PATENT DOCUMENTS

| | | | | |
|---|---|---|---|---|
| 4,233,977 | A * | 11/1980 | Mattson | A61F 5/4407 604/335 |
| 5,545,154 | A * | 8/1996 | Oberholtzer | A61F 5/443 604/336 |
| 5,672,163 | A * | 9/1997 | Ferreira | A61F 5/441 604/333 |
| 5,968,024 | A * | 10/1999 | Freeman | A61F 5/4407 604/323 |
| 6,267,506 | B1 * | 7/2001 | Campion | A45C 11/22 383/89 |
| 6,336,918 | B1 * | 1/2002 | Olsen | A61F 5/4407 604/355 |
| 6,419,664 | B1 * | 7/2002 | von Bulow | A61F 5/4407 604/327 |
| 6,589,221 | B1 * | 7/2003 | Olsen | A61F 5/4405 604/332 |
| 6,726,667 | B2 * | 4/2004 | Leise, Jr. | A61F 5/445 604/335 |
| 6,780,172 | B2 * | 8/2004 | Olsen | A61F 5/4407 604/332 |
| 6,858,023 | B2 * | 2/2005 | Poulsen | A61F 5/4407 604/335 |
| 6,887,222 | B2 * | 5/2005 | Mandzij | A61F 5/4407 604/277 |
| 7,223,260 | B2 * | 5/2007 | Hansen | A61F 5/4407 604/338 |
| 7,306,581 | B2 * | 12/2007 | Falconer | A61F 5/4407 604/339 |
| 7,842,018 | B2 * | 11/2010 | Schena | A61F 5/445 604/344 |
| 7,879,016 | B2 * | 2/2011 | Mandzij | A61F 5/4407 4/144.1 |
| 7,947,025 | B2 * | 5/2011 | Buglino | A61F 5/445 604/335 |
| 8,206,364 | B2 * | 6/2012 | Schertiger | A61F 5/4407 604/327 |
| 8,449,511 | B2 * | 5/2013 | Andersen | A61F 5/443 604/326 |
| 8,500,707 | B2 * | 8/2013 | Murray | A61F 5/445 383/88 |
| 8,672,907 | B2 * | 3/2014 | Friske | A61F 5/4407 604/335 |
| 8,821,463 | B2 * | 9/2014 | Grum-Schwensen | A61F 5/443 604/332 |
| 8,888,760 | B2 * | 11/2014 | Andersen | A61F 5/44 604/335 |
| 8,905,987 | B2 * | 12/2014 | Murray | A61F 5/445 383/57 |
| 9,629,744 | B2 * | 4/2017 | Villefrance | A61F 5/4405 |
| 9,668,910 | B2 * | 6/2017 | Murray | A61F 5/4407 |
| 10,813,786 | B2 * | 10/2020 | Lysgaard | A61F 5/4404 |
| 11,039,950 | B2 * | 6/2021 | Jones, Jr. | A61F 5/442 |
| 11,065,144 | B2 * | 7/2021 | Nielsen | A61F 5/4407 |
| 2003/0028160 | A1 * | 2/2003 | Leise, Jr. | A61F 5/445 604/334 |
| 2003/0073962 | A1 * | 4/2003 | Olsen | A61F 5/445 604/327 |
| 2003/0167042 | A1 * | 9/2003 | Poulsen | A61F 5/4407 604/327 |
| 2004/0049837 | A1 * | 3/2004 | Falconer | A61F 5/4407 383/88 |
| 2004/0171999 | A1 * | 9/2004 | Andersen | A61F 5/445 604/332 |
| 2005/0131360 | A1 * | 6/2005 | Villefrance | A61F 5/445 604/332 |
| 2005/0159717 | A1 * | 7/2005 | Holtermann | A61F 5/4407 604/332 |
| 2006/0111682 | A1 * | 5/2006 | Schena | A61F 5/442 604/334 |
| 2007/0265588 | A1 * | 11/2007 | Pedersen | A61F 5/4407 604/340 |
| 2008/0033379 | A1 * | 2/2008 | Pedersen | A61F 5/4407 604/335 |
| 2008/0051743 | A1 * | 2/2008 | Falconer | A61F 5/4407 604/277 |
| 2008/0097360 | A1 * | 4/2008 | Andersen | A61F 5/4407 604/332 |
| 2009/0082743 | A1 * | 3/2009 | Buglino | A61F 5/4405 604/335 |
| 2009/0143755 | A1 * | 6/2009 | Schertiger | A61F 5/445 29/428 |
| 2011/0028923 | A1 * | 2/2011 | Murray | A61F 5/4405 604/332 |
| 2011/0028924 | A1 * | 2/2011 | Murray | A61F 5/4407 604/332 |
| 2012/0022477 | A1 * | 1/2012 | Grum-Schwensen | A61F 5/443 604/332 |
| 2014/0005619 | A1 * | 1/2014 | Andersen | A61F 5/4404 604/332 |
| 2017/0209297 | A1 * | 7/2017 | Lysgaard | A61F 5/4404 |
| 2018/0333290 | A1 * | 11/2018 | Jones | A61F 5/445 |
| 2019/0029868 | A1 * | 1/2019 | Grum-Schwensen | A61F 5/4407 |
| 2019/0328572 | A1 * | 10/2019 | Weinberg | A61F 5/445 |
| 2020/0214872 | A1 * | 7/2020 | Tretheway | A61F 5/443 |
| 2020/0214873 | A1 * | 7/2020 | Tretheway | A61F 5/4407 |
| 2020/0214875 | A1 * | 7/2020 | Tretheway | A61F 5/448 |
| 2020/0229962 | A1 * | 7/2020 | Torstensen | A61F 5/4407 |
| 2020/0281761 | A1 * | 9/2020 | Tretheway | A61F 5/4404 |
| 2021/0100679 | A1 * | 4/2021 | Hoggarth | A61F 5/448 |
| 2021/0244564 | A1 * | 8/2021 | Jones, Jr. | A61F 5/441 |

FOREIGN PATENT DOCUMENTS

| | | | | |
|---|---|---|---|---|
| EP | 1511448 | B1 | 9/2006 | |
| EP | 1471856 | B1 | 3/2009 | |
| EP | 1791503 | B1 | 4/2009 | |
| EP | 1496820 | B9 | 2/2012 | |
| EP | 2268239 | B1 | 10/2016 | |
| EP | 2408405 | B1 | 8/2017 | |
| JP | 2006043037 | A * | 2/2006 | A61F 5/445 |
| JP | 2006043037 | A | 2/2006 | |
| WO | 2017222762 | A1 | 12/2017 | |
| WO | WO-2017222762 | A1 * | 12/2017 | A61F 5/442 |
| WO | 2018136793 | A1 | 7/2018 | |
| WO | 2020226861 | A1 | 11/2020 | |
| WO | 2021165705 | A1 | 8/2021 | |

OTHER PUBLICATIONS

Written Opinion issued by ISA/EPO in connection with PCT/US2023/060551 dated Mar. 20, 2023.

* cited by examiner

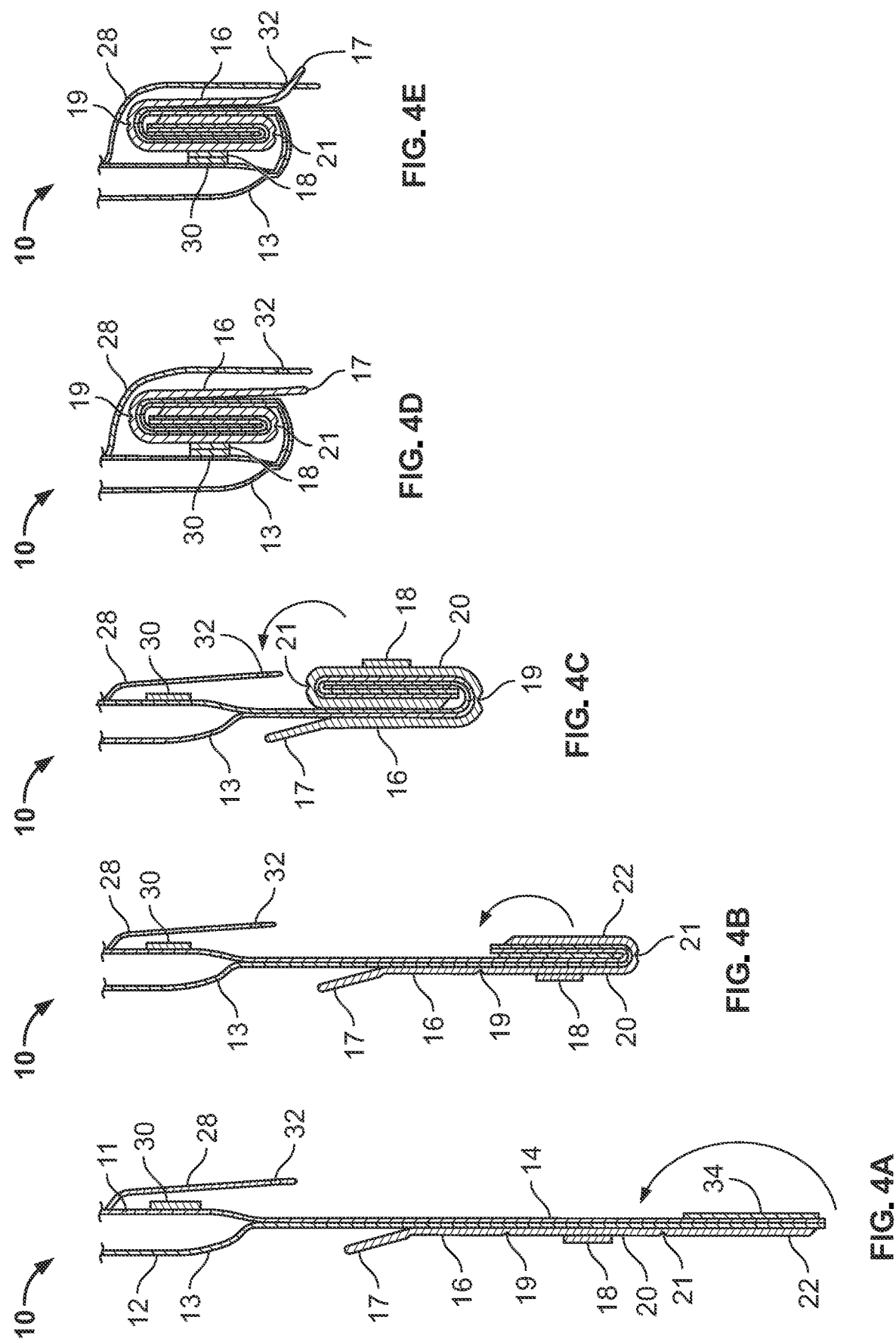

OUTLET CLOSURE AND SECUREMENT SYSTEM FOR DRAINABLE POUCH

This is a National Stage Application of International Patent Application No. PCT/US2023/060551, filed Jan. 12, 2023, which claims the benefit of and priority to U.S. Provisional Application No. 63/304,998, filed Jan. 31, 2022, the entirety of which are incorporated fully herein by reference.

BACKGROUND

The present disclosure pertains to a drainable pouch. More particularly, the present disclosure pertains to a system for securing a drainable pouch outlet.

Ostomy pouches for collecting body waste are used by patients who have had surgery such as a colostomy, ileostomy, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that body waste discharged through the stoma is received within the cavity.

The ostomy pouch may be a closed-end pouch for a single use, in which case the entire pouch is discarded after it has been substantially filled with stomal discharge. Alternatively, the ostomy pouch can be a drainable pouch with a discharge opening at its lower end, which may be closed during collection of body waste material but may be opened for draining body waste material from the pouch after a period of use. The discharge opening of drainable pouches is typically defined at the end of a narrowed outlet portion, which is provided with closure means for maintaining the discharge opening in a sealed condition until waste material is to be drained from the pouch.

For quality of life of the users, drainable pouches should be easy to drain without risking soiling of clothes or the surroundings. They also should be easy to close securely after being drained and amenable to being cleaned after drainage and before closing again, such that the risk of unpleasant odor is substantially reduced. Most importantly, the closure means should provide a secure seal when closed to minimize the risk of leakage. Further, it is also desirable that the closure means provide discretion for users.

Accordingly, there is a need for an improved system to close and secure a drainable pouch outlet.

SUMMARY

An outlet closure and securement system for drainable pouch is provided according to embodiments. The outlet closure and securement system may include a cover with at least one slot and at least one tab to secure and cover an outlet portion of the drainable pouch.

In one aspect, a drainable pouch may include a body side wall and a distal wall joined along their peripheral edges to define a cavity therebetween for collecting body waste, a downwardly extending outlet portion terminating in a discharge opening for draining body waste collected in the cavity, at least one tab and at least one slot configured to receive the at least one tab. The at least one tab may be attached to one of the pouch walls and the at least one slot may be arranged on a cover. The at least one tab may be received in the at least one slot when the outlet portion is folded up in a closed position.

In an embodiment, the at least one slot may be defined in a cover, which may be attached to the distal wall, while the at least one tab may be attached to the body side wall. The outlet portion may be configured to be folded up at least two times in the closed position, wherein the outlet portion in the closed position may be secured to and hidden behind the cover.

In an embodiment, the drainable pouch may further include a comfort layer attached to the distal wall. In such an embodiment, the cover may be integrally formed with the comfort layer.

In an embodiment, the cover layer may be formed from a fabric, a non-woven, a polymeric film, a laminate material comprising a fabric and a polymeric film, or a laminate material comprising a non-woven and a polymeric film.

In an embodiment, the cover may be sealed to the distal wall above the outlet portion. The cover may be configured to cover the outlet portion in the closed position when the at least one tab is received in the at least one slot.

In an embodiment, the outlet portion may include a closure member and a two-part fastening system comprising first and second fastening strips configured for securing the outlet portion in the closed position. The closure member may be attached to the body side wall. In such an embodiment, the at least one tab may be integrally formed with the closure member.

In some embodiments, the first fastening strip may be attached to the closure member and the second fastening strip may be attached to the distal wall under the cover.

In an embodiment, the drainable pouch may be configured to be closed by folding up the outlet portion three times. In such an embodiment, the closure member may include first, second, and third fold sections, wherein the first fold section may be folded toward the distal wall at a first fold, the second fold section may be folded toward the distal wall at a second fold, and the third fold section may be folded toward the distal wall at a third fold. The first and second fastening strips may be engaged, and the at least one tab may be received in the at least one slot after the third fold. The folded up and closed outlet portion may be hidden behind the cover. In an embodiment, the at least one tab may include a single tab extending from the third folding section, and the at least one tab may include a single tab.

Other aspects and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings.

FIG. 4A is a schematic cross-sectional view of the outlet portion of the ostomy pouch of FIG. 1 in an open position.

FIG. 4B is a schematic cross-sectional view of the outlet portion of the ostomy pouch of FIG. 1 folded up once.

FIG. 4C is a schematic cross-sectional view of the outlet portion of the ostomy pouch of FIG. 1 folded up two times.

FIG. 4D is a schematic cross-sectional view of the outlet portion of the ostomy pouch of FIG. 1 folded up three times and secured in place with a pair of fastening members and a cover.

FIG. 4E is a schematic cross-sectional view of the outlet portion of the ostomy pouch of FIG. 1 folded up three times and secured in place with a pair of fastening members, a cover, and tab through a slot.

DETAILED DESCRIPTION

Figure 1:
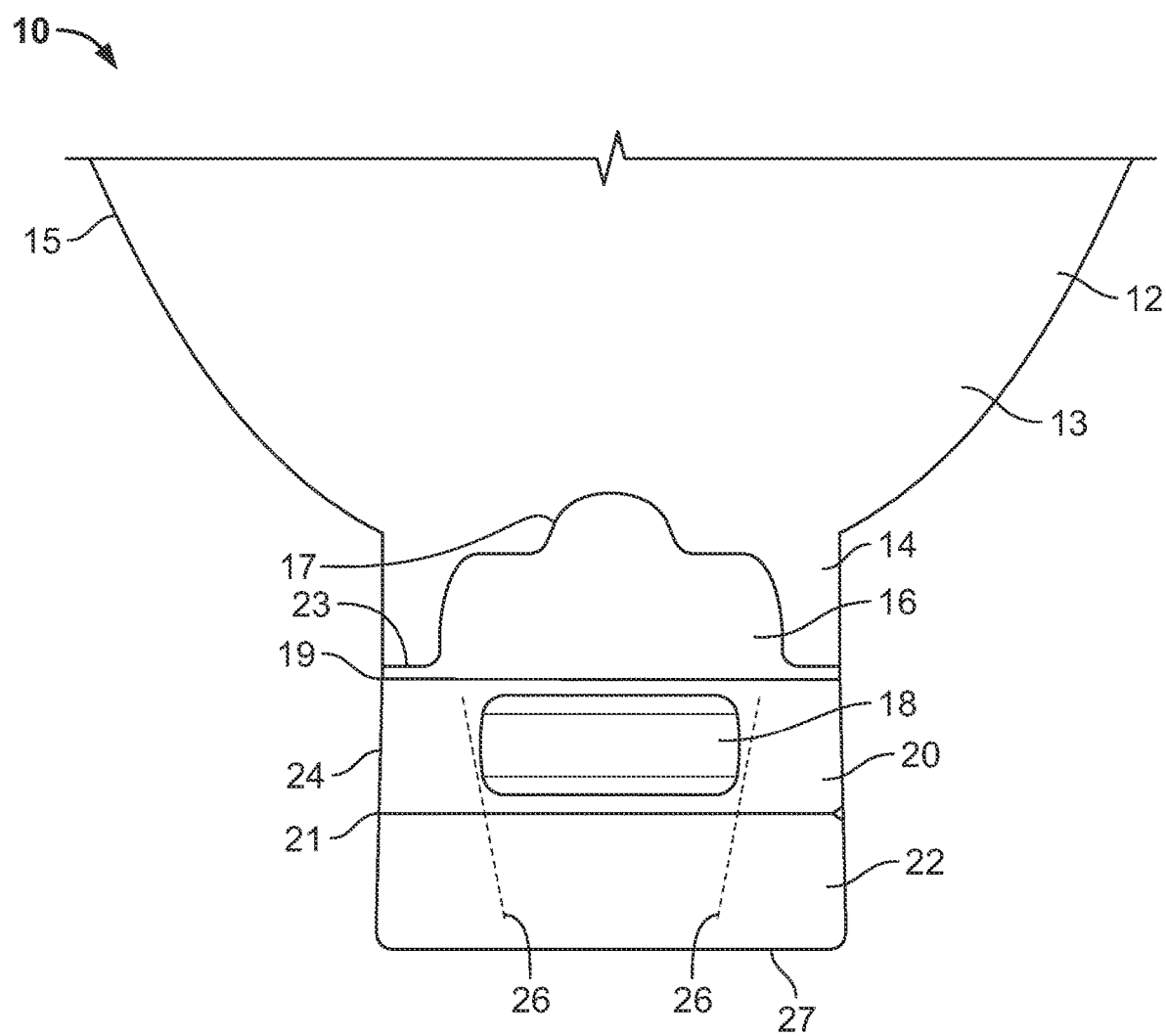
FIG. 1 is a body side view of an outlet portion of an ostomy pouch, according to an embodiment of the present disclosure.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

The present disclosure provides a drainable ostomy pouch that may include an outlet closure and securement system. The outlet closure and securement system may include a tab and a slot for securely and easily closing the drainable pouch.

Figure 2:
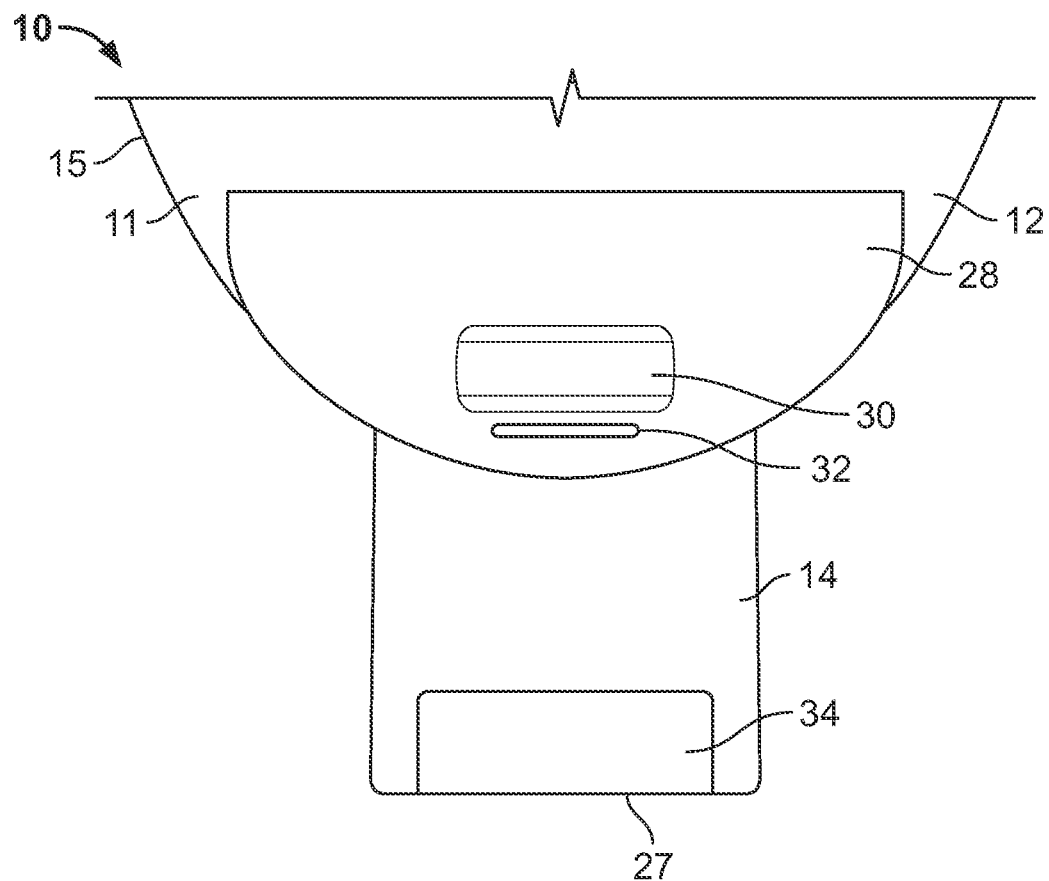
FIG. 2 is a distal side view of the outlet portion of the ostomy pouch of FIG. 1 in an open position.
Figure 3:
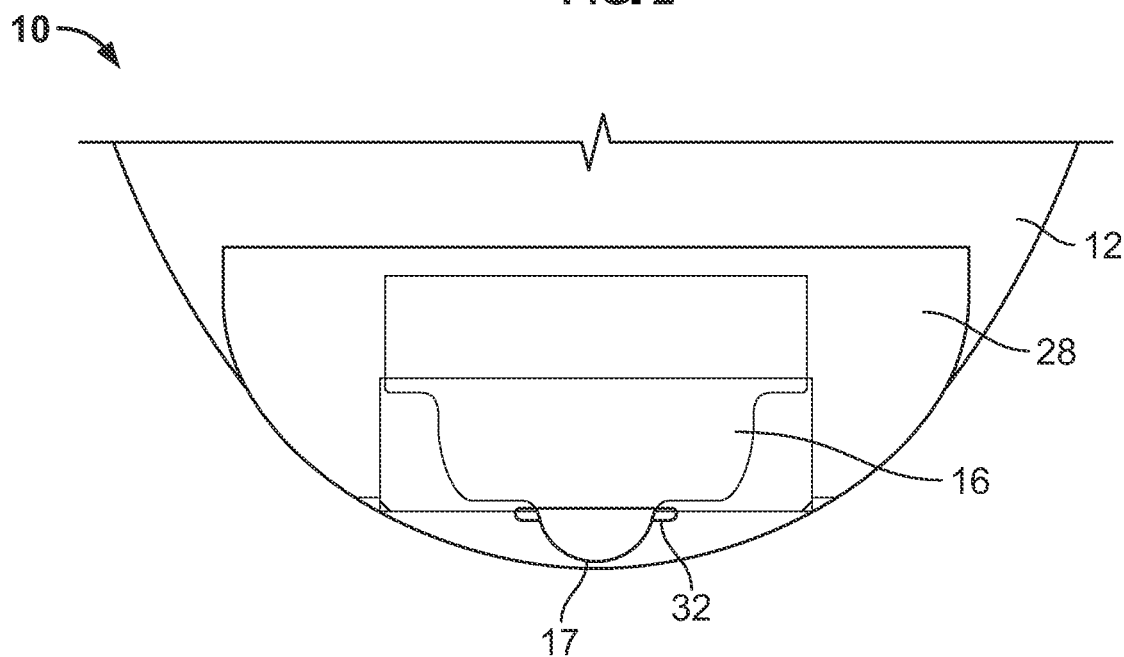
FIG. 3 is a distal side view of the outlet portion of the ostomy pouch of FIG. 1 in a closed position.

Referring now to the figures, FIGS. 1-4E show a drainable pouch 10 according to an embodiment. The drainable pouch 10 may include a distal wall 11 and a body side wall 13, which may be joined along their peripheral edges 15 to define a cavity therebetween for collecting stomal discharge. The drainable pouch 10 may include a downwardly extending outlet portion 14 terminating in a discharge opening 27 for draining the contents collected in the cavity after a period of use. The discharge opening 27 of the drainable pouch 10 may be closed during use by folding the outlet portion 14 upwardly and securing it in the upwardly folded position as shown in FIGS. 3 and 4E. The drainable pouch 10, for example, may be a drainable ostomy pouch.

FIGS. 1 and 2 show a body side view and a distal side view of an outlet portion of the drainable ostomy pouch 10, respectively. The drainable pouch 10 may generally include a collection portion 12, an outlet portion 14, a tab 17, a cover 28 including a slot 32, a closure member 24, fastener strips 18, 30, and a discharge opening 27. In an embodiment, the closure member 24 may be formed as a single-piece device including a first fold section 22, second fold section 20 and a third fold section 16. The third fold section 16 may be formed integrally with the closure member 24, such that the closure member 24 and the third fold section 16 are provided as a single-piece device. In such an embodiment, the closure member 24 may include a first transversely extending fold line 21 defined between the first and second fold sections 22, 20 and a second transversely extending fold line 19 defined between the second fold section 20 and the third fold section 16, which are configured to facilitate folding up and closing of the outlet portion 14. The closure member 24 may also include vertically extending or slanted fold lines 26 configured to facilitate opening of discharge opening 27 by allowing closure member 24 to bend outwardly at the fold lines 26.

In the embodiment of FIG. 1, the drainable pouch 10 includes one tab 17 configured to be received in the slot 32 to secure the outlet portion 14 in a folded up and closed position. In this embodiment, the tab 17 is integrally formed with the closure member 24 extending from the third fold section 16. In other embodiments, the tab 17 may be a separately formed from the closure member 24. In some embodiments, the drainable pouch 10 may not include a closure member 24 and at least one tab 17 may be attached to a pouch surface in or proximate the outlet portion. In an embodiment, drainable pouch 10 may include at least one tab 17 and at least one slot 32 configured to receive the at least one tab 17. For example, the cover 28 may include two slots 32 for accepting at least one tab 17.

In an embodiment, the drainable pouch 10 may include two tabs and two slots. The two tabs may be arranged at different locations.

In other embodiments, the first, second, and third fold sections 22, 20, 16 may be formed as three individual members and separately attached to a body side surface of the outlet portion 14. In some embodiments, the third fold section 16 and the second fold section 20 may be integrally formed as a single-piece device. In an embodiment, the tab 17 maybe formed integrally with the closure member 24 and configured to be inserted into the slot 32 when the outlet portion 14 is folded up in a closed position as shown in FIG. 3.

The closure member 24 may be formed from a suitable thin material, such as thin polymeric materials having a thickness of about 2 mil to about 40 mil, preferably about 5 mil to about 20 mil, and more preferably about 8 mil to about 15 mil. In an embodiment, the tab 17 may be made out of the same material as closure member 24.

In an embodiment, the drainable pouch 10 may be provided with at least one tab 17 attached to a body-side surface and at least one slot 32 provided on a distal side surface. In the embodiment of FIGS. 1 and 2, the single-piece closure member 24 including the tab 17 may be attached to a body side surface of the outlet portion 14, and the cover 28 including the slot 32 may be attached to a distal surface of the drainable pouch 10.

The first transversely-extending fold-line 21 may be arranged between the first fold section 22 and the second fold section 20 and may be configured to allow the outlet portion 14 to be folded up such that the first fold section 22 is arranged on the distal side of the outlet portion 14 after a first fold as shown in FIG. 4B. The second transversely-extending fold-line 19 may be arranged between the second fold section 20 and the third fold section 16 and may be configured to allow the outlet portion 14 to be folded up such that the first and second fold sections 22, 20 are arranged on the distal side of the outlet portion 14 after a second fold as shown in FIG. 4C.

The closure member 24 including the transversely-extending fold-lines 19, 21 and the fold lines 26 may provide two axis of manipulation including a transverse axis for folding and sealing, and an axial axes for opening of the drainable pouch 10. The transversely-extending fold-lines 19 and 21 and the axially-extending fold lines 26 may be defined by creases or cuts in the closure member 24. For example, the fold lines may be provided by cutting into the closure member 24 via any known method, such as via laser cutting or die cutting. Alternatively, the fold lines may be defined by living hinges formed during a molding or extrusion process of the one-piece closure member 24, each of which may comprise creases on both distal surface and pouch-facing surface of the closure member. In some embodiments, a closure member 24 may include three separately formed fold members 20, 22, 16, wherein transversely-extending fold-lines 19, 21 may be defined by spaces between the fold members 20, 22, 16.

FIG. 2 shows a distal side view of the outlet portion of the drainable ostomy pouch 10 of FIG. 1 in an open position. As shown in FIG. 2, the drainable pouch 10 may include the cover 28 including the slot 32 defined therein, a second fastener strip 30, and an optional stiffening member 34 on the distal side. The cover 28 may be formed from a suitable material, such as non-woven, fabric, polymeric materials and the like. In an embodiment, the cover 28 may be formed from a non-woven or fabric material of a desired color to provide discretion when the outlet portion 14 is folded up and secured under the cover 28 as shown in FIG. 3. In another embodiment, the cover 28 may be made out of a translucent material to allow the user to see that the outlet portion 14 is closed and secured under the cover 28.

In an embodiment, the optional stiffening 34 may be made out of the same material as the closure member 24.

FIG. 3 shows a distal side view of the outlet portion of the drainable ostomy pouch 10 of FIG. 1 in a closed position.

FIG. 4A shows a schematic cross-sectional view of the outlet portion of the drainable ostomy pouch 10 of FIG. 1 in an open position. Specifically, the drainable pouch 10 may include the collection portion 12, outlet portion 14, cover 28 with slot 32, first and second fastener strips 18, 30, closure member 24 including first, second, and third fold sections 22, 20, 16 and tab 17, and stiffening member 34, and a discharge opening 27. The drainable pouch 10 may be configured to be closed by folding up the outlet portion 14 three times toward a distal surface and engaging the first and second fastener strips 18, 30. The first and second fastener strips 18 and 30 may include fastener elements, which are adapted for releasable interlocking engagement.

To close the outlet portion 14, the outlet portion 14 may be folded toward a distal surface of the drainable ostomy pouch 10 along the transversely-extending fold-lines 19, 21. In this embodiment, the drainable ostomy pouch 10 may be configured to be closed and hidden by folding up the outlet portion 14 three times, engaging the fastening members 18, 30, concealing under the cover 28, and engaging the slot 32 with tab 17, thereby securing the outlet portion 14 in the closed and hidden position as shown in FIGS. 4A-4E. In other embodiments, the drainable ostomy pouch may be configured to be closed after folding up the outlet portion once or twice or more than three times.

In an embodiment, the first and second fastener strips 18 and 30 may comprise a hook and loop type of fasteners and/or pressure sensitive adhesives. By using the first and second fastener strips 18 and 30, the discharge opening 27 can be maintained in a closed position absent a disengagement force sufficient to overcome the retention force.

In an embodiment, the outlet securement system may include the cover 28 attached to the distal side of the pouch 10 proximately above the outlet portion 14, and the tab 17 attached to a body-side of the pouch on the outlet portion 14. The cover 28 may include the slot 32 defined therein configured to receive the tab 17. The securement system may be configured such that when the outlet portion 14 is folded up in a closed position, the tab 17 is received in the slot 32 and the folded-up outlet portion 14 is secured to and hidden behind the cover 28 as shown in FIGS. 3 and 4E.

In an embodiment, the cover 28 may be formed from a separate piece of comfort layer fabric, film, or a combination that is die-cut and sealed in position to the pouch. For example, the cover 28 may be formed from a laminated material comprising a non-woven and a polymeric film or a laminated material comprising a fabric and a polymeric film.

In an embodiment, the drainable pouch 10 may include a comfort layer attached to the distal pouch wall 11 and/or body side wall 13, wherein the cover 28 may be integrally formed with the comfort layer. In such an embodiment, the cover 28 may only be sealed to the pouch above the outlet portion 14, allowing for coverage of the outlet portion 14 when folded up and closed.

In an embodiment, the tab 17 may be configured to fit through the slot 32 in the cover 28, and the slot 32 may be configured to receive the tab 17, such that the cover 28 may cover the outlet portion 14 in a closed position. The slot 32 may be an opening in the cover material that allows the tab 17 to fit through.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A drainable pouch, comprising:
  a body side wall and a distal wall joined along their peripheral edges to define a cavity therebetween for collecting body waste;
  a downwardly extending outlet portion terminating in a discharge opening for draining body waste collected in the cavity;
  at least one tab attached to one of the body side wall and the distal wall; and
  at least one slot configured to receive the at least one tab arranged on the other of the body side wall and the distal wall;
  wherein the at least one tab is received in the at least one slot when the outlet portion is folded up in a closed position.

2. The drainable pouch of claim 1, wherein the at least one slot is defined in a cover, wherein the cover is attached to the distal wall and the at least one tab is attached to the body side wall.

3. The drainable pouch of claim 2, wherein the outlet portion is configured to be folded up at least two times in the closed position, wherein the outlet portion in the closed position is secured to and hidden behind the cover when the at least one tab is received in the at least one slot.

4. The drainable pouch of claim 2, wherein the outlet portion is configured to be folded up once in the closed position, wherein the outlet portion in the closed position is secured to and hidden behind the cover when the at least one tab is received in the at least one slot.

5. The drainable pouch of claim 2, wherein the outlet portion is configured to be folded up at least three times in the closed position, wherein the outlet portion in the closed position is secured to and hidden behind the cover when the at least one tab is received in the at least one slot.

6. The drainable pouch of claim 2, further including a comfort layer attached to the distal wall, wherein the cover is integrally formed with the comfort layer.

7. The drainable pouch of claim 2, wherein the cover is formed from a fabric or a non-woven.

8. The drainable pouch of claim 2, wherein the cover is formed from a polymeric film material.

9. The drainable pouch of claim 2, wherein the cover is formed from a laminate material comprising a fabric and a polymeric film or a laminate material comprising a non-woven and a polymeric film.

10. The drainable pouch of claim 2, wherein the cover is sealed to the distal wall above the outlet portion.

11. The drainable pouch of claim 2, wherein the cover is configured to cover the outlet portion in the closed position when the at least one tab is received in the at least one slot.

12. The drainable pouch of claim 2, wherein the outlet portion includes a closure member and a two-part fastening system comprising first and second fastening strips configured for securing the outlet portion in the closed position.

13. The drainable pouch of claim 12, wherein the closure member is attached to the body side wall on the outlet portion, and the at least one tab is integrally formed with the closure member.

14. The drainable pouch of claim 12, wherein the first fastening strip is attached to the closure member and the second fastening strip is attached to the distal wall under the cover.

15. The drainable pouch of claim 12, wherein the closure member includes first, second, and third fold sections, wherein the drainable pouch is configured to be closed by folding up the outlet portion three times, wherein the first fold section is folded toward the distal wall at a first fold, the second fold section is folded toward the distal wall at a second fold, and the third fold section is folded toward the distal wall at a third fold, and the first and second fastening strips are engaged and the at least one tab is received in the at least one slot after the third fold, and wherein the folded up and closed outlet portion is hidden behind the cover.

16. The drainable pouch of claim 12, wherein the at least one tab includes a single tab extending from the third folding section and the at least one tab includes a single tab.

* * * * *